United States Patent

(12) United States Patent
Gupta et al.

(10) Patent No.: US 8,654,334 B1
(45) Date of Patent: Feb. 18, 2014

(54) INCOHERENT CAVITY RINGDOWN SPECTROSCOPY GAS ANALYZER COUPLED WITH PERIODIC CHEMICAL SCRUBBING

(75) Inventors: Manish Gupta, Mountain View, CA (US); J. Brian Leen, Sunnyvale, CA (US); Douglas Steven Baer, Menlo Park, CA (US)

(73) Assignee: Los Gatos Research, Mountain View, CA (US)

( * ) Notice: Subject to any disclaimer, the term of this patent is extended or adjusted under 35 U.S.C. 154(b) by 117 days.

(21) Appl. No.: 13/347,440

(22) Filed: Jan. 10, 2012

Related U.S. Application Data

(60) Provisional application No. 61/553,373, filed on Oct. 31, 2011.

(51) Int. Cl.
G01N 21/00 (2006.01)

(52) U.S. Cl.
USPC .......................................................... 356/437

(58) Field of Classification Search
None
See application file for complete search history.

(56) References Cited

U.S. PATENT DOCUMENTS 5,272,345 A * 12/1993 Durham et al. ................ 250/373
7,679,059 B2 * 3/2010 Zhou ............................. 250/343

OTHER PUBLICATIONS

A. O'Keefe et al., "Cavity ring-down optical spectrometer for absorption measurements using pulsed laser sources", Review of Scientific Instruments, 59, 1988, 11 pages.

P.L. Kababian et al., "A practical alternative to chemiuluminescence-based detection of nitrogen dioxide: cavity attenuated phase shift spectroscopy", Enviro. Science & Tech., vol. 42, No. 16, 2008, pp. 6040-6045.
J.J. Scherer et al., "Broadband ringdown spectral photography", Applied Optics, vol. 40, No. 36, Dec. 20, 2001, pp. 6725-6732.
A.O'Keefe et al., "Cavity ring-down optical spectrometer for absorption measurements using pulsed laser sources", Review of Scientific Instruments, 59, 1988, pp. 2544-2554.
D.S. Medina et al., "Detection of sulfur dioxide by cavity ring-down spectroscopy", Environ. Sci. Tech., dx.doi.org/10.1021/es103739r, 6 pages, Nov. 7, 2010.
D.S. Medina et al., "Detection of sulfer dioxide by cavity ring-down spectroscopy", supporting information of dx.doi.org/10.1021/es2010-03739r, 5 pages.
M. Buhr et al., Development and field testing of a small, efficient, photolytic converter for measurement of ambient nitrogen dioxide (NO2), 2008 Nat'l Air Quality Conference, Apr. 8, 2008, 11 pages.

(Continued)

*Primary Examiner* — Gregory J Toatley
*Assistant Examiner* — Amanda Merlino
(74) *Attorney, Agent, or Firm* — Law Offices of Thomas Schneck

(57) ABSTRACT

An incoherent cavity ringdown spectroscopy (iCRDS) gas analyzer is provided with a gas flow path to introduce a sample gas into an enclosed volume bounded by a pair of mirrors defining an optical cavity. A pulsed broadband incoherent light source with a wavelength band that coincides with an absorption band of a specified gas species to be detected (e.g., NO2 or SO3) directs pulses of light into the optical cavity, while a photodetector is positioned to detect light exiting the cavity. A scrubber in an alternate flow path into the enclosed volume periodically scrubs the sample gas of the specified gas species. A processor determines the concentration of the specified gas species from the ringdown decay time of the photodetector measurement signals, with the periodic scrubbing of the sample gas providing a calibration reference from its slower decay time.

13 Claims, 3 Drawing Sheets

(56) References Cited

OTHER PUBLICATIONS

L. Biennier et al., "Multiplex integrated cavity output spectroscopy of cold PAH cations", Chem. Physics Letters, 387, 2004, pp. 287-294.

J.B. Paul et al., "Ultrasensitive absorption spectroscopy with a high-finesse optical cavity and off-axis alignment", Applied Optics, vol. 40, No. 27, Sep. 20, 2001, pp. 4904-4910.

P. Castellanos et al., "Modification of a commercial cavity ring-down spectroscopy NO2 detector for enhanced sensitivity", Review of Scientific Instruments, 80, 113107, 2009, 6 pages.

J.M. Langridge et al., "A compact broadband cavity enhanced absorption spectrometer for detection of atmospheric NO2 using light emitting diodes", The Analyst, 2006, 131, pp. 916-922.

D.S. Baer et al., "Sensitive absorption measurements in the near-infrared region using off-axis integrated-cavity-output spectroscopy", Applied Physics B, 2002, doi:10.1007/s00340-002-0971-z, 5 pages.

"Integrated science assessment for oxides of nitrogen-heath criteria", U.S. Environmental Protection Agency, EPA/600/R-08/071, Jul. 2008, 20 pages.

G. Berden et al., "Cavity ring-down spectroscopy: experimental schemes and applications", Reviews in Physical Chemestry, 2000, vol. 19, No. 4, pp. 565-607.

D. Mihelcic et al., "An improved method of measuring tropospheric NO2 and RO2 by matrix isolation and electron spin resonance", Journal of Atmospheric Chemistry, 3, 1985, pp. 341-361.

Abstract only: J.S. Gaffney et al., "Aircraft measurements of nitrogen dioxide and peroxyacyl nitrates using luminol chemiluminescence with fast capillary gas chromatography", Environ. Science Tech., 1999, 33, 19, pp. 3285-3289.

Abstract only: H. Fuchs et al.., "A sensitive and versatile detector for atmospheric NO2 and NOx based on blue diode laser cavity ring-down spectroscopy", Environ. Science Tech., 2009, 43, 20, pp. 7831-7836.

Abstract only: S.T. Sandholm et al., "An airborne compatible photogragmentation two-photon laser-induced fluorescence instrument for measuring background tropospheric levels of NO, NOx, and NO2", Journal of Geophysical Research, vol. 95, No. D7, pp. 10, 155-10, 161,1990.

* cited by examiner

INCOHERENT CAVITY RINGDOWN SPECTROSCOPY GAS ANALYZER COUPLED WITH PERIODIC CHEMICAL SCRUBBING

CROSS-REFERENCE TO RELATED APPLICATION

This application claims priority from U.S. provisional application No. 61/553,373, filed Oct. 31, 2011.

TECHNICAL FIELD

The present invention relates to gas analyzers for measuring the concentration of one or more specified gas species in a gaseous sample.

BACKGROUND ART

Nitrogen dioxide ($NO_2$) is a secondary by-product of the combustion processes found in almost all vehicles and power plants. The high-temperatures and very reactive chemical species found in combustion form nitric oxide (NO) from oxidation of $N_2$ and fuel nitrogen. This NO then rapidly oxidizes in the atmosphere to form $NO_2$.

There is substantial scientific evidence that links short-term $NO_2$ exposure (30 minutes-24 hours) to respiratory illness (e.g. asthma and possibly emphysema) and cardiovascular mortality, with a strong correlation between $NO_2$ levels and hospital admissions for respiratory problems. $NO_2$ susceptibility is particularly high for at-risk (e.g. children, elderly, and those with respiratory issues) and underserved communities. Additionally, $NO_2$ measurements serve as a general indicator of total nitrogen oxide ($NO_x$) concentrations. $NO_x$, in turn, reacts with atmospheric constituents (e.g. ammonia, water and volatile organic compounds to form small particulates and ground-level ozone respectively, which can lead to premature death, lung tissue damage, and respiratory diseases.

Due to the adverse effects of short-term $NO_2$ exposure and recent scientific verification, the EPA has established an annual, average $NO_2$ standard of 53 $ppb_v$ (=100 $\mu g/m^3$), strengthened the primary, 1-hour NAAQS for $NO_2$ to 100 $ppb_v$, and is making changes in the air quality monitoring network to focus on locations with maximum $NO_2$ concentrations [Environmental Protection Agency, 40 CFR Parts 50 and 58, Feb. 9, 2010, "Primary National Ambient Air Quality Standards for Nitrogen Dioxide; Final Rule," *Federal Register* 75 (26) 6473]. The monitoring network will now include analyzers near major roadways in urban areas, community-wide measurements in large population centers, and additional sensors in particularly vulnerable communities. Future $NO_2$ standards may be even more stringent, with the World Health Organization recommending an annual compliance standard of 21 $ppb_v$ (=40 $\mu g/m^3$), and the California Air Resources Board approving a level of 30 $ppb_v$.

Likewise, sulfur dioxide ($SO_2$) is a major atmospheric pollutant. Once in the atmosphere it is oxidized in the gas phase and in clouds to form sulfuric acid ($H_2SO_4$) and leads to the production of aerosol sulfate, the deposition of which contributes to acidification of the surrounding ecosystem. Typical concentrations have fallen in recent years to less than 50 $\mu g/m^3$ (18.8 ppb) in most areas, but in certain conditions can exceed 24-hour average levels of 100 $\mu g/m^3$ (37.6 ppb) with peak concentrations over 500 $\mu g/m^3$ (188 ppb) at times. The U.S. Environmental Protection Agency has set a primary standard of 75 ppb for the average 1-hour daily maximum concentration of sulfur dioxide [75 FR 35520, Jun. 22, 2010].

The World Health Organization has set a 24-hour average interim target level (IT-1) for sulfur dioxide of 125 $\mu g/m^3$ (47.0 ppb) and a guideline level of 20 $\mu g/m^3$ (7.5 ppb).

Currently, the EPA Test Method approved for $NO_2$ detection (e.g. Method 7E) involves catalytic reduction followed by chemiluminescence. The ambient air sample is first reacted with ozone to convert nitric oxide into excited nitrogen dioxide:

$$NO + O_3 \rightarrow NO_2^* + O_2.$$

The excited $NO_2^*$ then deactivates via visible luminescence that can be detected by a photomultiplier tube. Quantification of the emitted intensity provides a measurement of the NO concentration. The air sample is then passed over a hot, catalytic surface (e.g., Mo at 375° C.) to reduce $NO_2$ to NO, and the chemiluminescence detector sees an additional signal due to the increase of NO. The concentration of $NO_2$ can then be determined from the difference in luminescence before and after catalytic reduction.

There are several disadvantages to this measurement strategy. Foremost, the hot catalytic surface also converts a variety of other ambient nitrogen-containing, air species (e.g. peroxy acetyl nitrate, alkyl nitrates, $HNO_3$ . . . ) into NO. Therefore, chemiluminescence detectors substantially overestimate $NO_2$ concentrations (by as much as a factor of 2), a critical limitation as compliance standard levels are further decreased. EPA has recognized this problem [U.S. EPA, "Integrated Science Assessment for Oxides of Nitrogen—Health Criteria," EPA/600/R-07/093] and suggested that such detectors are better suited to detect the total concentration of nitrogen oxides ($NO_x$).

A number of alternative strategies have been proposed to more accurately measure ambient $NO_2$ concentrations:

Photolytic Chemiluminescence

Instead of using a hot catalyst, photolysis near 300-400 nm can be used to convert $NO_2$ into NO (and ozone) [M. Buhr, "Development and Field Testing of a Small, Efficient, Photolytic Converter for Measurement of Ambient Nitrogen Dioxide," 2008 National Air Quality Conference, Apr. 8, 2008]. This method is much more specific to $NO_2$ and avoids interferences from other atmospheric, nitrogen-containing compounds. However, the conversion efficiency is not well-characterized and can vary over time as the photolysis source and gas residence time change. Moreover, the photolysis source typically operates at a relatively high radiant flux, thus limiting its lifetime to ~5000 hours (208 days of continuous operation). Finally, though the instruments are relatively cost-effective (e.g. ~$20 k with photolytic converter), they require significant labor (e.g. calibration and maintenance) and toxic consumables (e.g. $O_3$, NO).

Luminol Chemiluminescence

Alternatively, luminol can react with $NO_2$ to form an excited state that subsequently luminesces [J. S. Gaffney et al., "Aircraft Measurements of Nitrogen Dioxide and Peroxyacyl Nitrates Using Luminol Chemiluminescence with Fast Capillary Gas Chromatography" *Environ. Sci. Technol.* 33 (19) 1999, 3285]. Although this technique does not require conversion of $NO_2$ into NO, it is not linear at low $NO_2$ concentrations and exhibits cross-interferences with peroxy acetyl nitrate.

Mid-Infrared Tunable Diode Laser Absorption Spectrometry (TDLAS)

A tunable laser operating near 6.23 μm can also be used to very accurately quantify ambient $NO_2$ concentrations using absorption spectrometry. Although this technique is very selective and accurate, it is prohibitively expensive (e.g. $80-$120 k retail) and insufficiently robust for compliance monitoring applications.

There are also a host of more complicated, laboratory-based measurement techniques for $NO_2$, including electron spin resonance [D. Mihelcic, P. Musgen, and D. H. Ehhalt, *J. Atmos. Chem.* 3, 341 (1985)], laser-induced fluorescence and differential optical absorption spectrometry [S. T. Sandholm, J. D. Bradshaw, K. S. Dorris, M. O. Rodgers, and D. D. Davis, *J. Geophys. Res., [Atmos.]* 95, 10155 (1990)]; however, these technologies are still primarily limited to laboratory instrumentation.

More recently, visible cavity-enhanced optical absorption methods have been used to accurately quantify ambient $NO_2$ concentrations using both lasers and light emitting diodes (LEDs). Cavity ringdown spectroscopy (CRDS) near 400-532 nm has been used by a variety of research groups to achieve a measurement precision of better than ±40 ppt, with minimal interferences from other atmospheric species [P. Castellanos et al., *Rev. Sci. Instrum.* 80 (2009) 113107; and H. Fuchs et al., *Environ. Sci. Technol.* 43 (2009) 7831]. Similarly, Integrated Cavity Output Spectroscopy (ICOS) [J. Langridge et al., *Analyst* 131 (2006) 916] and Cavity Attenuated Phase shift Spectroscopy (CAPS) [P. L. Kebabian et al., *Environ. Sci. Technol.* 42 (2009) 6040] have attained comparable results.

Recently, cavity ring-down spectroscopy has been used to detect sulfur dioxide down to 3.5 ppb concentrations, employing a frequency-doubled dye laser at 308 nm wavelength as a coherent light source for the optical cavity [David S. Medina, Yingdi Liu, Liming Wang, and Jingsong Zhang, "Detection of sulfur dioxide by cavity ring-down spectroscopy", *Environ. Sci. Technol.* 45(5) (Mar. 1, 2011) 1926-31].

SUMMARY DISCLOSURE

A gas analyzer that is highly sensitive and selective for the particular gas species to be measured (such as $NO_2$) combines incoherent Cavity Ringdown Spectroscopy (iCRDS) with an autonomous, periodic chemical scrubber. Unlike most of the aforementioned prior methods, the present analyzer, when analyzing $NO_2$ in a gas sample, is unaffected by other nitrogen species and does not require consumable gases, making it an ideal alternative for compliance monitoring. The combination of iCRDS with chemical scrubbing provides for a low-cost, compact instrument (iCRDS benefits) with no need for or use of any calibration reference samples (periodic chemical scrubbing benefit).

A method of measuring the concentration of a specified gas species (such as $NO_2$ or $SO_2$) in a gaseous sample (such as the ambient atmosphere) operates by inputting the gaseous sample into an optical cavity and directing pulses of incoherent light (e.g. from a light emitting diode) of a specified wavelength band (e.g. in a neighborhood of 404 nm for $NO_2$ and near 308 nm for $SO_2$) off-axis into the optical cavity. The wavelength band coincides with an absorption band of the specified gas species being measured. The intensity of light output from the optical cavity is detected and the decay time of that intensity is measured. The decay time corresponds to the concentration of the gas species in the gaseous sample. In order to provide a suitable reference against extraneous background absorption of the light, the gaseous sample is periodically scrubbed (e.g. with a chemical scrubber) to intentionally remove the specified gas species from the sample. Measuring the decay time with the gas species absent from the sample forms a calibration reference, thereby allowing more accurate determination of the concentration of the gas species in the sample.

DETAILED DESCRIPTION

In conventional cavity ringdown spectroscopy [A. O'Keefe and D. A. G. Deacon, *Rev. Sci. Instrum.*, 59, 2544 (1988)], a gas sample is introduced into a high-finesse optical cavity comprised of two highly-reflective mirrors (R>99.99% typical). A laser beam passes through the mirror in order to enter the cavity and is detected by passing through the output mirror. If the light is of the correct frequency, it constructively interferes with itself and builds up in the optical cavity. When the intensity has built up sufficiently, the laser is rapidly blocked and the decay of light intensity out of the cavity is measured. If the system is well aligned, this decay will be exponential (FIG. 3) with a time constant $\tau$ that depends on all losses the in the cavity:

$$\tau = \frac{L}{c}((1-R)+\sigma L)^{-1},$$

where L is the cell length, c is the speed of light, R is the mirror reflectivity, $\sigma$ is the coefficient of optical loss due to absorption by the gas.

The advantage of CRDS is that the effective pathlength of the absorbing species is dependent on the reflectivity of the mirrors, $L_{eff}=L/(1-R)$, and, for highly reflective mirrors (R~99.99%) the effective pathlength approaches 10,000 meters! This enormous effective pathlength allows for very small absorptions to give rise to detectable changes in the decay time $\tau$. Moreover, since $\sigma$ is an absolute measure of cavity loss, CRDS gives an absolute measure of gas absorption without need for calibration or an offline measurement. Due to these advantages, CRDS has since led to over 400 publications worldwide [G. Berden et al., *Int. Rev. Phys. Chem.* 19 (2000) 565], and is emerging as a powerful analytical tool for trace gas detection.

The major limitations of conventional CRDS are its stringent alignment requirements, and the need to match the laser source and the optical modes of the high finesse cavity. In order to detect very small changes in a, it is necessary to have the laser focused properly into the cavity ("mode-matched") and to have the optical cavity very stable and well aligned. To match the narrowband frequency of the laser source to an optical mode of the cavity (and thus achieve coupling of the light and actual throughput), one must either dither the frequency of the laser or mechanically adjust the cavity length to produce resonance. These limitations have made it difficult to produce robust instrumentation based on CRDS.

Figure 1:
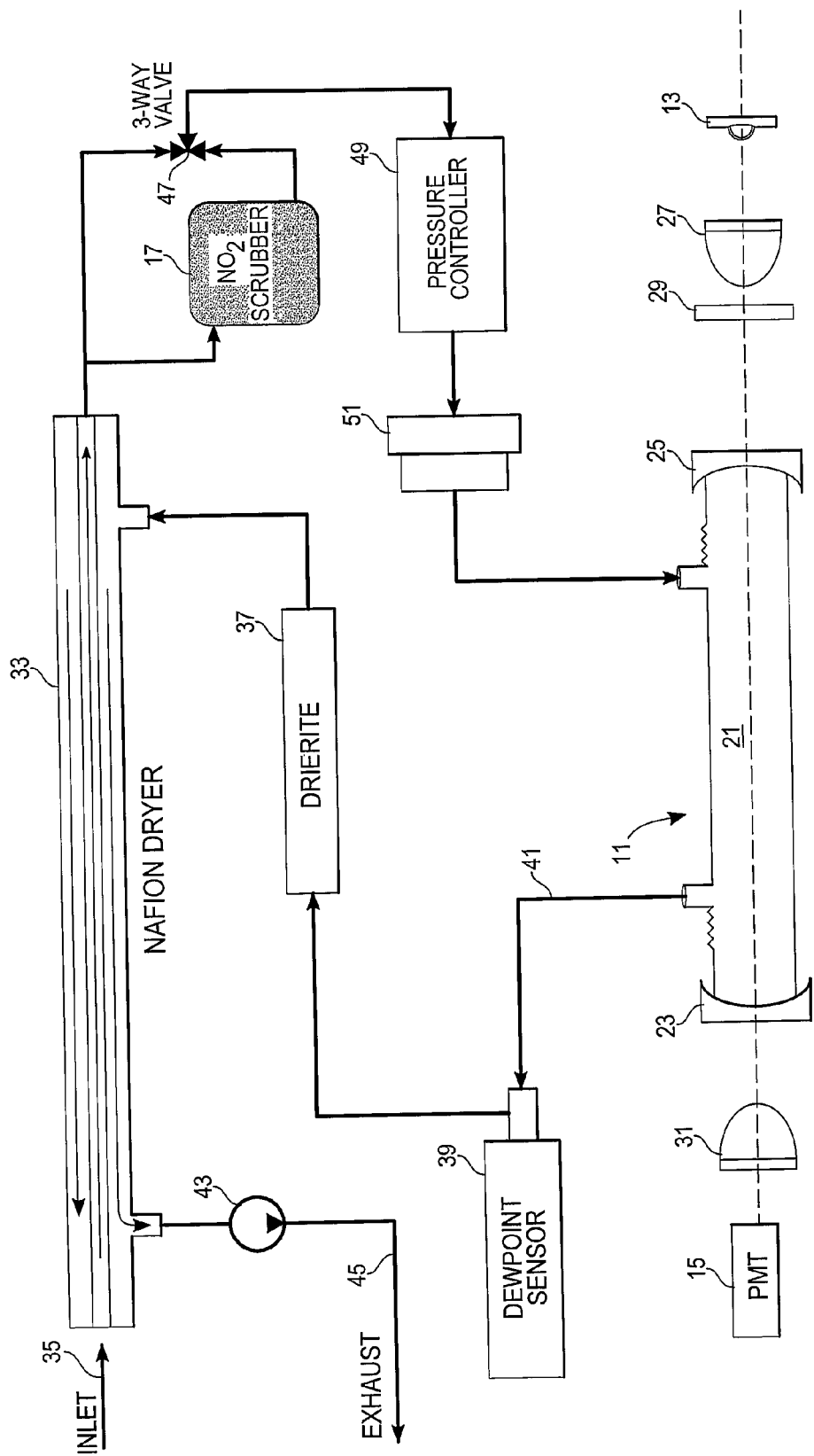
FIG. 1 is a schematic plan view of an incoherent off-axis cavity ringdown spectroscopy gas analyzer in accord with the present invention.

With reference to FIG. 1, incoherent Cavity Ringdown Spectroscopy (iCRDS) represents a very simple solution to these problems and is ideally suited for detection of broadband absorbers (e.g. $NO_2$). Instead of trying to spatially and spectrally couple a single-frequency laser into a high-finesse optical cavity 11, a broadband, incoherent light source 13 is utilized. This source 13 (e.g. lamp, broadband laser, or LED) couples into a myriad of cavity modes and the incoherent photons do not show any constructive or destructive interference (e.g. similar to the present assignee's Off-Axis ICOS technique described in U.S. Pat. No. 6,795,190) [D. S. Baer et al., "Sensitive absorption measurements in the near-infrared region using off-axis integrated-cavity-output spectroscopy," invited paper *Appl. Phys. B* 75 (2002) 261]. The net result is a system that can tolerate a high degree of mechanical instability (e.g. very robust) without requiring any specialized locking electronics.

Several research groups, including Los Gatos Research, Inc. of Mountain View, Calif., helped pioneer iCRDS [J. J. Scherer et al., *Appl. Opt.* 40 (2001) 6725; and L. Biennier et al., *Chem. Phys. Lett.* 387 (2004) 287] and the technique has been used to measure a wide array of atmospheric constituents. As noted above, variants of the technique have recently been used to quantify $NO_2$ using LEDs, broadband diode lasers and Off-Axis CRDS (in which a coherent laser is coupled to a high-finesse cavity in an incoherent fashion). In the present invention, we combine a broadband LED 13 operating near 405 nm ('near' being, e.g., ±10 nm) to make iCRDS measurements of $NO_2$ with periodic scrubbing to provide background measurement of cavity loss. The scrubbing may be conducted with a chemical scrubber 17 provided prior to input of the gaseous sample into the cavity 11. This technique has resulted in a compact, cost-effective $NO_2$ analyzer optimized for compliance monitoring.

Accordingly, an embodiment of the gas analyzer includes the optical cavity 11 having an enclosed volume 21 for receiving sample gas between two highly reflective mirrors (R>0.99%) 23 and 25. A typical analyzer device would have an optical cavity that is approximately 1 m in length with 50 cm focal length cavity mirrors. The enclosed volume may have diameter of approximately 6 mm. The incoherent broadband light source, such as LED 13, directs light into the cavity 11 through one of the two mirrors, e.g. mirror 25. A collimating lens 27 and bandpass filter 29 may be provided in the path between the LED 13 and cavity mirror 25 to provide a collimated beam and select that portion of the LED emission wavelength band that coincides with an absorption band the gas species to be detected (e.g. near 405 nm for $NO_2$). A photodetector 15, such as a photomultiplier tube (PMT), may be situated to receive light exiting the optical cavity 11 through one of the mirrors, e.g. mirror 23. A collection lens 31 may be provided between cavity mirror 23 and the detector 15 to concentrate the light for low-noise detection.

The gas sample is supplied to the optical cavity 11. Because water vapor is also an absorber of light, a nafion dryer 33 may be provided at the sample inlet 35 to remove water from the gaseous sample. The nafion dryer 33 typically contains a zeolite inner tube through which the gas sample passes. Drierite (anhydrous calcium sulfate) 37 or some other efficient water absorber substance then passes dry gas through an outer tube of the dryer 33. A dewpoint sensor 39 may be used to only pass gas into the nafion dryer 33 when necessary. The dry gas is typically the exhaust gas 41 from the optical cavity 11, that is, the same composition as the inlet sample, so that the measurement will not be affected by any transfer of the species to be measured across the zeolite tube of the dryer 33. A pump 43 drives the flow of gas from the inlet 35 to its eventual exhaust 45 after its use in the dryer 33.

Also, prior to introducing the sample gas to the optical cavity 11, the gas is periodically scrubbed of the gas species to be measured using a chemical scrubber 17. The scrubber may employ a reducer, such as ferrous sulfate, urea, aqueous ammonia, or sodium sulfide. A three-way valve 47 directs the dried gas either through the scrubber 17 for scrubbing, or along an alternate path that bypasses the scrubber 17. The valve 47 periodically switches the gas flow between the two available paths. A pressure controller 49 and a Teflon membrane filter 51 may also be provided to prevent damage to the cavity volume 21 or to mirrors 23 and 25 due to excessive pressure or unwanted particles.

Precision

Figure 2:
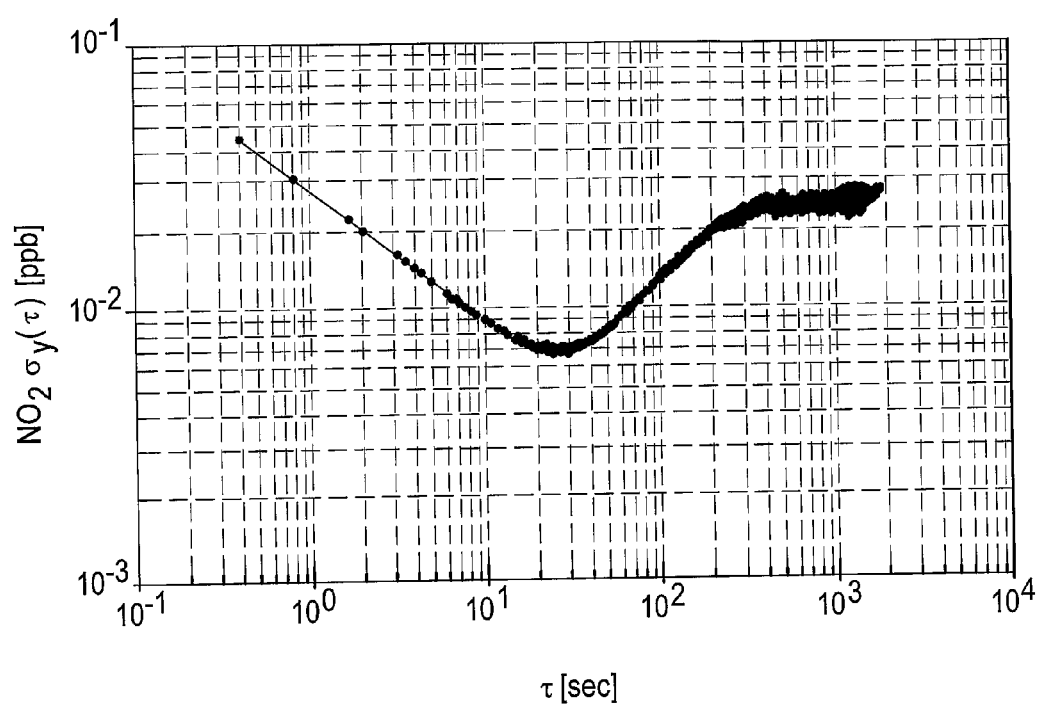
FIG. 2 is an Allan deviation plot graphing $NO_2$ concentration $\sigma_y(\tau)$ in parts per billion versus ringdown decay time $\tau$ in seconds.

The instrument measurement precision was empirically determined by measuring a $NO_2$-free air stream continuously for >8 hours. The resulting Allan deviation plot is shown in FIG. 2. The instrument exhibits a 5 Hz precision of ±0.043 $ppb_v$ ($1\sigma$). Moreover, it retains a measurement precision of <0.03 ppb (1$\sigma$) for over 30 minutes, the typical calibration interval of the unit (i.e. self-calibration based on using the $NO_2$ scrubber as indicated above). Thus, the sensor can quantify ambient $NO_2$ with a precision substantially better than ±0.1 ppb ($1\sigma$) for long-term compliance monitoring needs.

Calibrating the Instrument Via Controlled Dilutions of a NIST $NO_2$ Standard

Figure 3:
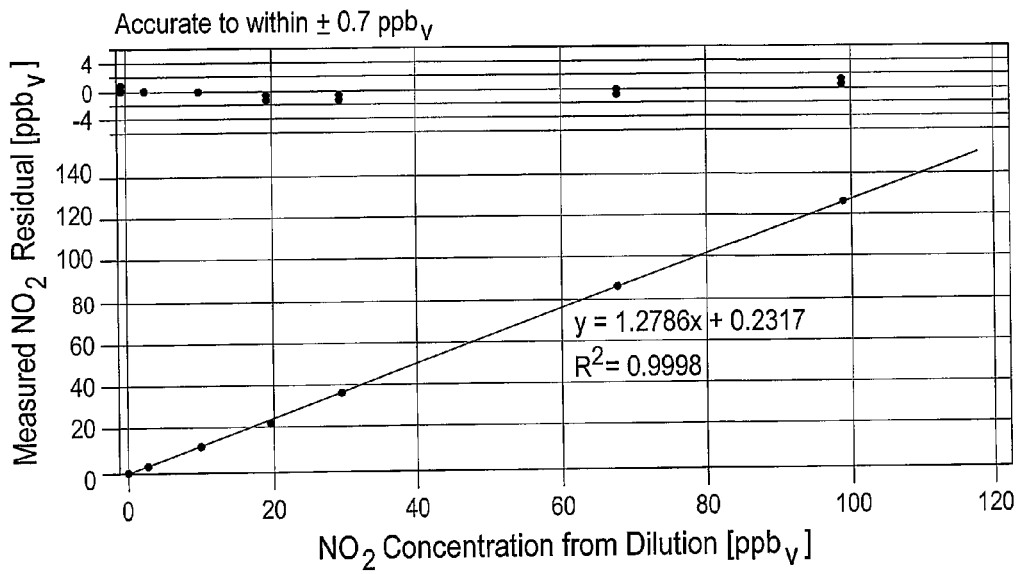
FIGS. 3 and 4 show calibration plots of measured $NO_2$ using the instrument of FIG. 1 versus $NO_2$ concentrations from dilution and from chemiluminescence measurement.

The instrument was calibrated by accurately diluting a $NO_2$ standard (165 $ppb_v$) from 0-100 $ppb_v$ in dry nitrogen. $NO_2$ concentration measured by the instrument versus the calculated $NO_2$ concentration from the dilution factors. The results of these tests are shown in FIG. 3. The instrument has a calibration factor of 1.2786, and exhibits excellent linearity ($R^2$=0.9998) and precision over this measurement range.

Taking the calibration factor into account, the instrument is accurate to ±0.7 $ppb_v$ ($1\sigma$) for $NO_2$ concentrations ranging from 0-100 $ppb_v$, well within the dilution error of ±1%.

Figure 4:
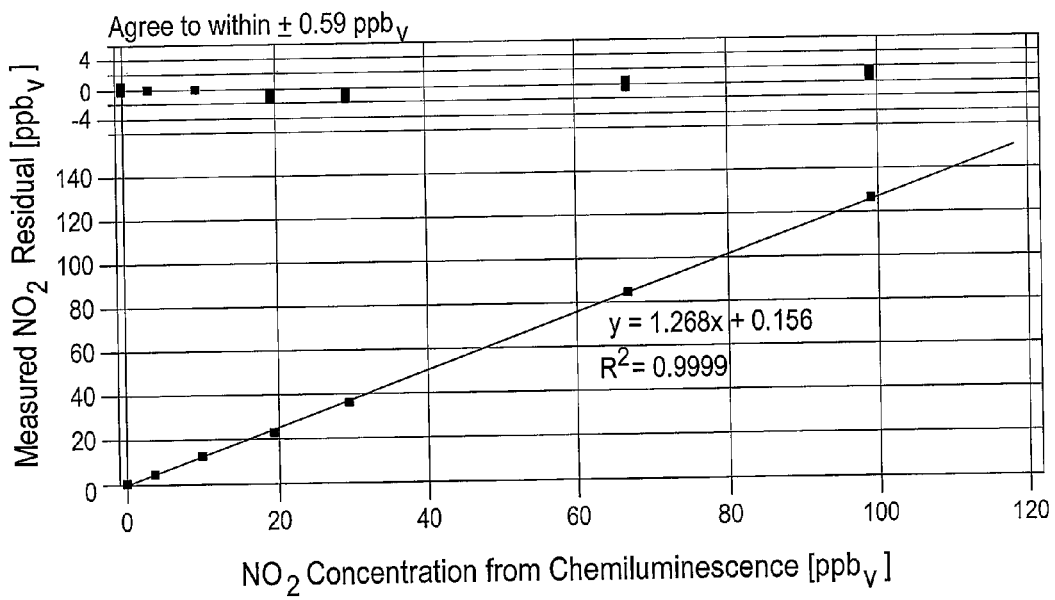

The output of the dilution system was simultaneously measured by a Thermo Scientific Model 42C Trace Level NO—$NO_2$—$NO_x$ Analyzer that utilizes chemiluminescence to detect $NO_2$. This analyzer is widely used in EPA applications to monitor $NO_2$, and it is one of the main replacement targets of the proposed instrument (due to its need for frequent calibration, consumables, and cross-interferences). The comparison data is shown in FIG. 4. It clearly indicates that the iCRDS instrument has a calibration factor of 1.268, which slightly lower than that determined by other methods due to $NO_2$ loss in the 42C. Once this factor has been accounted for, the instruments provide data that agrees to within ±0.59 $ppb_v$ ($1\sigma$) for $NO_2$ concentrations ranging from 0-100 $ppb_v$. Note that the comparison provides a slightly lower calibration factor of 1.268. This has been attributed to inaccuracies in the Thermo 42C analyzer.

The technique can be readily extended to a variety of other broadband absorbing species, including sulfur dioxide. For example, sulfur dioxide may be measured using an incoherent UV source emitting in a band that includes approximately 300 nm light. The periodic chemical scrubber may employ sodium carbonate to remove the $SO_2$ from the sample.

What is claimed is:

1. A method of measuring a concentration of a specified gas species within a gaseous sample, comprising:
inputting a gaseous sample into an optical cavity;
directing pulses of incoherent light of a specified wavelength band off-axis into the optical cavity, the wavelength band of the incoherent light coinciding with an absorption band of a gas species to be measured;

detecting an intensity of light output from the optical cavity and measuring a decay time of that intensity, the decay time corresponding to a concentration of the gas species in the gaseous sample; and periodically scrubbing the gaseous sample to remove any of the specified gas species from the sample and inputting the scrubbed sample into the optical cavity, a decay time of the intensity of light output from the cavity with the scrubbed gas forming a calibration reference for determining the concentration of the gas species in the gaseous sample.

2. The method as in claim 1, wherein the gaseous sample is taken from an ambient atmosphere.

3. The method as in claim 1, wherein the specified gas species is nitrogen dioxide ($NO_2$).

4. The method as in claim 3, wherein the wavelength band of the incoherent light includes a wavelength of 404 nm.

5. The method as in claim 1, wherein the specified gas species is sulfur dioxide ($SO_2$).

6. The method as in claim 5, wherein the wavelength band of the incoherent light includes a wavelength of 308 nm.

7. The method as in claim 1, wherein the pulses of incoherent light are provided by a light emitting diode (LED).

8. The method as in claim 1, wherein the periodic scrubbing of the gaseous sample is performed using a chemical scrubber.

9. A gas analyzer, comprising:
   an enclosed volume bounded by a pair mirrors defining an optical cavity therebetween;
   a gas flow path coupled to the enclosed volume to introduce a sample gas into the optical cavity;
   a pulsed broadband incoherent light source with a wavelength band coinciding with a specified gas species to be detected, the light source positioned to direct pulses of light into the optical cavity;
   a photodetector positioned to detect light exiting the optical cavity;
   a scrubber in an alternate flow path between the gas flow path and the optical cavity configured to periodically scrub the sample gas of the specified gas species; and
   a processor receiving measurement signals from the photodetector both when the sample gas is supplied directly to the optical cavity and when it is periodically scrubbed in the scrubber, the processor determining a concentration of the specified gas species from a ringdown decay time of the photodetector measurement signals.

10. The gas analyzer as in claim 9, wherein the specified gas species is nitrogen dioxide ($NO_2$) and the light source emits light in a band that includes a wavelength of 404 nm light.

11. The gas analyzer as in claim 9, wherein the specified gas species is sulfur dioxide ($SO_2$) and the light source emits light in a band that includes a wavelength of 308 nm.

12. The gas analyzer as in claim 9, wherein the light source is a light emitting diode.

13. The gas analyzer as in claim 9, wherein the photodetector is a photomultiplier tube.

* * * * *